United States Patent [19]

Kaiser et al.

[11] Patent Number: 4,461,309

[45] Date of Patent: Jul. 24, 1984

[54] IONYL-ALKYL AND IONYL ALKENYL ETHERS AS FLAVORANTS FOR TOBACCO

[75] Inventors: Roman Kaiser, Uster; Dietmar Lamparsky, Wangen-Dübendorf, both of Switzerland

[73] Assignee: Givaudan Corporation, Clifton, N.J.

[21] Appl. No.: 229,907

[22] Filed: Jan. 30, 1981

Related U.S. Application Data

[60] Continuation of Ser. No. 070,200, Aug. 27, 1979, abandoned, which is a division of Ser. No. 915,839, Jun. 15, 1978.

[30] Foreign Application Priority Data

Jun. 27, 1977 [LU] Luxembourg ............................ 77627
Apr. 26, 1978 [CH] Switzerland ......................... 4499/78

[51] Int. Cl.$^3$ .......................... A24B 3/12; A24B 15/30
[52] U.S. Cl. .................................................. 131/276
[58] Field of Search ................. 131/275, 276; 426/538

[56] References Cited

U.S. PATENT DOCUMENTS 3,899,597  8/1975  Mookherjee et al. .............. 426/538
3,993,664  11/1976  Thomas et al. .................. 426/538 X
3,996,296  12/1976  Mookherjee et al. .......... 426/538 X

OTHER PUBLICATIONS

Kandel et al., Amm. Chem., vol. 11, (1939), pp. 73–77, 120–125, 136–139, 142.
Arctander Perfume of F. Cav. Chem., 1969, Published by the Author Montclair, N. J., Item No. (1776–1778).

*Primary Examiner*—V. Millin
*Attorney, Agent, or Firm*—Robert F. Tavares

[57] ABSTRACT

Ionyl-alkyl and ionyl-alkenyl ethers as flavorants for tobacco.

5 Claims, No Drawings

IONYL-ALKYL AND IONYL ALKENYL ETHERS AS FLAVORANTS FOR TOBACCO

This is a continuation of application Ser. No. 070,200 filed Aug. 27, 1979 now abandoned which is a division of application Ser. No. 915,839 filed June 15, 1978.

FIELD OF THE INVENTION

This invention relates to the fields of perfumes and flavorants.

SUMMARY OF THE INVENTION

This invention relates to the hereinafter-more-specifically designated ionyl-alkyl ethers and ionyl alkenyl ethers and their use in perfume and flavoring compositions, as well as to a process for making and using said compositions.

DESCRIPTION OF THE PREFERRED EMBODIMENTS

The odorant and/or flavoring compositions provided by the present invention contain as essential odor- and/or flavor-imparting ingredient an effective amount of a compound of the general formula

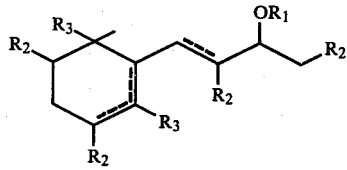

(I)

wherein $R_1$ represents a $C_{1-4}$-alkyl or $C_{2-4}$-alkenyl group, $R_2$ represents a hydrogen atom or the methyl group, $R_3$ represents the methyl or ethyl group, the broken line in the side-chain represents an optional bond and one of the broken lines in the ring represents an additional bond.

The foregoing formula is intended to embrace all possible geometric isomers having regard to the cis-/trans isomerism present.

The compounds of formula I have particular organoleptic properties, on the basis of which they are excellently suited as odorant and/or flavouring substances.

The invention is therefore also concerned with a method of imparting an odour and/or a flavour to materials, which method comprises applying to said materials or incorporating therein an odour- and/or flavour-imparting amount of a compound of formula I, especially in practically pure form or in the form of mixtures (with the exception of natural mixtures containing a compound of formula I), or of an odorant and/or flavouring composition containing same.

The expression "practically pure" is used herein to mean, in particular, a compound of formula I which is free from accompanying substances which are present besides compounds of formula I in natural extracts. As practically pure compounds of formula I in the scope of the present invention there should be understood, for example, synthetically manufactured compounds of formula I.

The compounds of formula I have a wide spectrum of olfactory nuances which is readily evident from Table I hereinafter. The compounds of formula I can therefore be used, for example, for the perfuming or flavouring of products such as cosmetics (soaps, toothpastes, mouth washes, deodorants, shampoos, lotions, ointments, powders etc), detergents or foodstuffs, beverages, drinks, e.g. soft drinks, and tobacco, the compounds preferably not being used alone but rather in the form of compositions which contain other odorant or flavouring substances.

The compounds of formula I, wherein the ether group is a $C_{1-3}$ ether group, are preferred.

Ionone derivatives of formula I are preferred, with those of the general formula

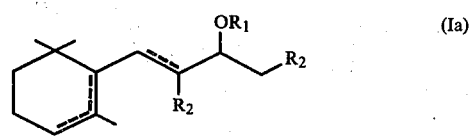

(Ia)

wherein $R_1$, $R_2$ and the broken lines have the significance given earlier, being especially preferred.

TABLE I
Examples of compounds of formula I

| | | odoriferous characterisation |
|---|---|---|
| 1 β-Ionyl methyl ether 2,6,6-Trimethyl-1-(3-methoxy-1-butenyl)-cyclohex-1-ene | | woody (raw wood), fruity (direction of raspberry), flowery. |
| 2 β-Ionyl ethyl ether 2,6,6-Trimethyl-1-(3-ethoxy-1-butenyl)-cyclohex-1-ene | | fruity (direction of apricot and raspberry) woody-cedarous, flowery. |
| 3 β-Ionyl isopropyl ether 2,6,6-Trimethyl-1-(3-isopropoxy-1-butenyl)-cyclohex-1-ene | | woody, flowery. |
| 4 β-Ionyl butyl ether 2,6,6-Trimethyl-1-(3-butoxy-1-butenyl)-cyclohex-1-ene | | woody, flowery. |
| 5 Dihydro-β-ionyl methyl ether 2,6,6-trimethyl-1-(3-methoxy-butyl)-cyclohex-1-ene | | fruity, woody-cedarous, earthy (humus). |
| 6 Dihydro-β-ionyl ethyl ether 2,6,6-Trimethyl-1-(3-ethoxy-butyl)-cyclohex-1-ene | | fruity-ester like (direction of pear skin), woody, ionone-like. |
| 7 α-Ionyl methyl ether 2,6,6-Trimethyl-1-(3-methoxy-butenyl)-cyclohex-2-ene | | dry, woody (direction of pine wood), balsamic. |

TABLE I-continued

Examples of compounds of formula I

| | | odoriferous characterisation |
|---|---|---|
| 8 α-Ionyl ethyl ether 2,6,6-Trimethyl-1-(3-ethoxy-1-butenyl)-cyclohex-2-ene | | dry, woody, fruity, ethereal. |
| 9 α-Iryl methyl ether 2,5,6,6-Tetramethyl-1-(3-methoxy-1-butenyl)-cyclohex-2-ene | | mellow, flowery, woody. |
| 10 12/13-Methyl-α-ionyl methyl ether 2,6-Dimethyl-6-ethyl-1-(3-methoxy-1-butenyl)-cyclohex-2-ene | | fresh, green, woody, slightly camphorous. |
| 11 3,6,6-Trimethyl-2-ethyl-1-(3-methoxy-1-butenyl)-cyclohex-2-ene | | flowery, woody, balsamic, aspects of tea and tobacco. |
| 12 Dihydro-α-ionyl ethyl ether 2,6,6-Trimethyl-1-(3-ethoxy-butyl)-cyclohex-2-ene | | fruity, flowery. |
| 13 cis-β-Ionyl methyl ether 2,6,6-Trimethyl-1-(3-methoxy-cis-1-butenyl)-cyclohex-1-ene | | camphorous, woody, sweetish. |
| 14 cis-β-Ionyl ethyl ether 2,6,6-Trimethyl-1-(3-ethoxy-cis-1-butenyl)-cyclohex-1-ene | | woody, balsamic, sweetish, powdery. |
| 15 Isomethyl-α-ionyl methyl ether 2,6,6-Trimethyl-1-(3-methoxy-2-methyl-1-butenyl)-cyclohex-2-ene | | woody, earthy, dry, ionone-like. |
| 16 β-Ionyl allyl ether 2,6,6-Trimethyl-1-(3-allyloxy-1-butenyl)-cyclohex-1-ene | | woody, spicy, slightly green, tobacco-like. |
| 17 Dihydro-β-ionyl allyl ether 2,6,6-Trimethyl-1-(1-allyloxy-butyl)-cyclohex-1-ene | | woody, spicy, slightly flowery, tobacco-like weaker than 16. |
| 18 Isomethyl-α-ionyl ethyl ether 2,6,6-Trimethyl-1-(3-ethoxy-2-methyl-1-butenyl)-cyclohex-2-ene | | pinewood-like, slightly fruity. |

On the basis of their high capability of blending harmoniously, the compounds of formula I are especially suitable as odorants, especially in combination with a series of natural and synthetic odorants or flavouring substances such as, for example:

galbanum oil, mastix oil, vetiver oil, patchouli oil, sandalwood oil, cedar oil, tree moss absolute, basil oil, camomile oil, angelica seed oil, star anis oil, rosemary oil, lavander oil, lavandin oil, palmarosa oil, sage oil, petitgrain oil, neroli oil, bergamotte oil, lemon oil, orange oil, grapefruit oil, geranium oil, rose oil, ylang-ylang oil, coriander oil, melilotus absolute, jasmine absolute, cassia absolute, narcissus absolute, violet leaf absolute, tuberose absolute, benzoin resinoid, frankincense resinoid, iris concrete etc;

aldehydes such as hydroxycitronellal, cyclamen aldehyde, p-tert.butyl-α-methylcinnamaldehyde, α-hexylcinnamaldehyde, 3,5-dimethyl-cyclohex-3-en-1-yl-carboxaldehyde, benzaldehyde, phenylacetaldehyde, vanillin, heliotropin, p-methoxybenzaldehyde, citral, citronellal, isovaleraldehyde, trans-2-hexenal, sorbic aldehyde, trans-2-cis-6-nonadienal, 2,4-decadienal, methylnonylacetaldehyde etc;

ketones such as α-ionone, β-ionone, methylionone, acetylcedrene, acetanisole, 4-(p-hydroxyphenyl)-2-butanone, nootkatone etc;

acetals and ketals such as phenylacetaldehyde dimethylacetal, 2-methyl-1,3-dioxolan-2-ethyl acetate, capronaldehyde diethylacetal etc;

ethers such as eugenol methyl ether, anethol, estragol, methyl 1-methylcyclododecyl ether etc;

phenolic compounds such as eugenol, isoeugenol etc;

alcohols such as butanol, cis-3-hexenol, trans-2-cis-6-nonadienol, linalool, geraniol, nerol, citronellol, α-terpineol, benzyl alcohol, phenylethyl alcohol etc;

esters such as methyl dihydrojasmonate, linalyl acetate, geranyl acetate, bornyl acetate, α-terpenyl acetate, cedryl acetate, santalyl acetate, ethyl 2-ethyl-3,6,6-trimethyl-2-cyclohexen-1-yl carboxylate, p-tert.butyl-cyclohexyl acetate, benzyl acetate, styrallyl acetate, phenylethyl acetate, dimethylbenzylcarbinyl butyrate, amyl salicylate, ethyl α-methylphenylglycidate, ethyl butyrate, butyl acetate, hexyl acetate, hexyl butyrate, cis-3-hexenyl butyrate, ethyl trans-2-hexenoate, ethyl trans-2-octenoate, ethyl 2,4-decadienate, heptynecarboxylic acid methyl ester etc;

lactones such as γ-undecalactone, γ-decalactone, γ-nonalactone, δ-decalactone, δ-octalactone, coumarin etc;

acids such as butyric acid, α-methylbutyric acid, trans-2-hexenoic acid etc;

sulphur-containing compounds such as p-menthane-8-thiol-3-one, sulphides (e.g. dimethylsulphide etc), disulphides, etc;

nitrogen-containing compounds such as methyl anthranilate, linalyl anthranilate, indole, isobutylquinoline etc; and compounds having a musk-like and amber-like odour such as 1,3,4,6,7,8-hexahydro-4,6,6,7,8,8-hexamethyl-cyclopenta-δ-2-benzopyran, 12-oxahexadecanolide, ethylene brassylate, 8α,12-oxido-13,14,15,16-tetranorlabdane etc.

The compounds of formula I can also be used in the reconstitution of essential oils, absolutes or other natural substrates, especially those which contain ionones as the olfactorily-relevant components (e.g. tobacco absolute, costus root oil, violet absolute, passion fruit extract, raspberry extract etc).

The compounds of formula I can accordingly be used for the production of compositions and, as will be evident from the foregoing, they can be used together with a wide range of known odorants. The compounds of formula I are especially useful for the production of compositions having flowery, fruity, woody, green, chypre-like and cologne-like notes. In the production of such compositions, the aforementioned known odorants can be used in a manner which is known to the perfumer; for example, as described by W. A. Poucher, Perfumes, Cosmetics and Soaps 2, 7, published by Chapman and Hall, London, 1974.

Thus, for example, the ethyl ether 2 is able to enrich flowery-fruity perfume compositions with additional radiation power and naturalness and thus comes to meet the tendencies of modern perfumery in a welcomed manner. The methyl ether 7 elevates the hesperidine note in fresh, citrus-like, woody compositions in an advantageous manner and at the same time underlines the woody character in an improved way. It can generally be stated that 2, for example, shows very good effects in distinctly feminine perfumes, while 7 is used with advantage in masculine compositions. On the other hand, interesting flower complexes can also be produced with the aid of 7 and 2 combines well with pine-wood notes.

The remaining ionyl ethers lie, in relation to their effects in perfume compositions, approximately between the ethyl ether 2 and the methyl ether 7 (see Table I).

The concentration of the compounds of formula I can vary within wide limits depending on the purpose of use; for example, between about 0.01 wt.% in the case of detergents and about 15 wt.% in the case of alcoholic solutions. In perfume bases or concentrates the concentration can, of course, also be higher. The perfume bases can be used in the customary manner for the perfuming of Eau de Cologne, eau de toilette, lotions, creams, shampoos, soaps, toothpastes, detergents etc.

With low concentrations (e.g. 0.5%-2%) of compounds of formula I there can already be established a distinct increase in the radiance without the basic character of the composition being substantially altered. With high concentrations (e.g. 10%-30%) there also sets in a modification corresponding to the olfactory properties of the particular compound used without the individual odour of the ether being, however, penetrated.

As flavouring substances, the compounds of formula I can be used, for example, for the production or improvement, intensification, enhancement or modification of fruit or berry aromas in foodstuffs (yoghurt, sweet goods etc), in beverages, e.g. tea, in drinks, e.g. soft drinks (lemonades, etc) and in tobacco.

When used as flavouring substances, the compounds of formula I have an invigorating effect and c der natural notes.

The pronounced flavour qualities of especially practically pure, and particularly of synthetically manufactured, compounds of formula I enable them to be used in low concentrations. A suitable range is, for example, 0.01 ppm-100 ppm, preferably 0.1 ppm-20 ppm in the finished product (i.e. the flavoured foodstuff, luxury consumable or drink).

In the flavouring of, for example, tobacco, the concentration can, however, also be higher and can have a wider range; for example, a range of 1 ppm-1000 ppm, preferably 50 ppm-500 ppm.

In Table II hereinafter there are compiled some effects which can be achieved with the compounds of formula I.

TABLE II

| Compound | Aroma | Concentration | Effect |
|---|---|---|---|
| 1,2 | Raspberry | ppm in the finished product 0.01-100 ppm especially 0.1-20 ppm | greater naturality, fruit character full flavour |
| 1,2 | Peach | ppm in the finished product 0.01-100 ppm especially 0.1-20 ppm | very natural fruit character, aspect of the fruit skin is restored well |
| 1,2 | Apricot | ppm in the finished product 0.01-100 ppm especially 0.1-20 ppm | very natural fruit character, aspect of the fruit skin is restored well |
| 5,7,15 | Bilberry | ppm in the finished product 0.01-100 ppm especially 0.1-20 ppm | very natural fruit character, typical earthy, woody aspect comes into play well |
| 1,2,6 | Tobacco | ppm in the finished product 1-1000 ppm especially 50-500 ppm | upon smoking a pleasant woody and slight flowery note, more pleasant and rounded-off flavour |

TABLE III

Flavouring properties of compounds of formula I in 5% sugar water

| Compound | Concentration ppm | Flavouring characterisation |
|---|---|---|
| 1 | 5 | woody, fruity, certain aspects of the raspberry restored |
| 2 | 5 | as 1, but additional velvety nuance reminiscent of the fruit skin of peach and apricot |
| 5 | 3 | earthy, woody, fruity, reminiscent of bilberries |
| 6 | 2 | fruity, ester-like, slightly woody, reminiscent of pear skins |
| 7 | 5 | woody, balsamic, slightly ionone-like |
| 8 | 2 | acts woody and dry, reminiscent of juniper berries |
| 15 | 1 | fruity, woody, slightly earthy and ionone-like, certain aspects of the raspberry and bilberry |
| 16 | 5 | spicy, reminiscent of dried fruit |

The compounds of formula I can be mixed with the ingredients used for flavouring compositions or added to such flavourants in the usual manner. Among the flavourants contemplated in accordance with the present invention there are to be understood flavouring compositions which can be diluted or dispersed in edible materials in a manner known per se. They can be converted according to methods known per se into the usual forms of use such as solutions, pastes or powders. The products can be spray-dried, vacuum-dried or lyophilised.

The known flavouring substances which are conveniently used in the production of such flavourants are either referred to hereinbefore or can readily be obtained from the literature such as, for example, J. Merory, Food Flavorings, Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press, Inc., Cleveland, Ohio, 1975.

For the production of such usual forms of use there come into consideration, for example, the following carrier materials, thickening agents, flavour-improvers, spices, auxiliary ingredients etc:

Gum arabic, tragacanth, salts or brewers yeast, alginates, carrageen or similar absorbents; indoles, maltol, dienals, spice oleoresins, smoke flavours; cloves; diacetyl, sodium citrate; monosodium glutamate, disodium inosine-5'-monophosphate (IMP), disodium guanosine-5-phosphate (GMP); or special flavouring substances, water, ethanol, propyleneglycol, glycerine.

With the exception of the methyl ether 7 and the ethyl ether 8 (Ann. Chim. 11, 73–142 [1939]), the compounds of formula I are novel compounds. The novel compounds of formula I also form part of the present invention.

The compounds of formula I can be prepared in a manner known per se, namely by alkylating or alkenylating the alcoholates produced from the corresponding alcohols of the general formula

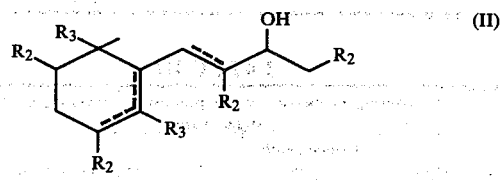

wherein $R_2$, $R_3$ and the broken lines have the significance given earlier, (see, for example, Organikum, Organisch-chemisches Grundpraktikum, 9. Aufl. VEB Deutscher Verlag der Wissenschaften, Berlin 1969, 222 et seq).

Especially suitable alkylating agents are dialkyl sulphates and alkyl bromides. The alcoholates are conveniently produced by reacting the alcohols with an alkali metal (e.g. sodium or potassium) or an alkali metal hydride (e.g. sodium hydride) in an inert solvent such as benzene, toluene, xylene etc.

The following Examples illustrate the manner in which the compounds of formula I hereinbefore can be prepared:

EXAMPLE 1

A solution of 60.0 g (0.31 mol) of β-ionol in 100 ml of benzene was added to a suspension of 16.7 g (0.38 mol) of sodium hydride (55%–60% in mineral oil) in 500 ml of benzene and the mixture was subsequently stirred at reflux for 20 hours. The alcoholate suspension was now cooled down to 30° C. and treated over a period of 30 minutes with 50.5 g (0.40 mol) of dimethyl sulphate in such a manner that the temperature did not exceed 50° C. Subsequently, the mixture was stirred at reflux for 3 hours, cooled to room temperature, cautiously treated with 15 ml of methanol and, after 10 minutes, with 300 ml of 2-N aqueous sodium hydroxide and again stirred at room temperature for 2 hours. The organic phase of the cooled mixture was washed with water until neutral, dried over sodium sulphate and concentrated. The residual 70.0 g of material were subjected to a crude distillation in the presence of 0.5 g of anhydrous soda. Fine distillation of the crude β-ionyl methyl ethyl 1 (42 g) over a 20 cm Widmer column gave 38.5 g (60.0%) of pure and olfactorily good product of boiling point 56°–57° C./0.02 mmHg.

IR: 1198, 1139, 1108, 1082, 970, 850 cm$^{-1}$;

NMR: 1.00 (6H, 2s); 1.28 (3H, d, J~6.5 Hz); 1.69 (3H, s); 6.30 (3H, s); 3.77 (1H, m); 5.30 (1H, dxd, $J_{HAHX}$~7.5 Hz, $J_{HAHB}$~16 Hz); 6.10 (1H, d, J~16 Hz)

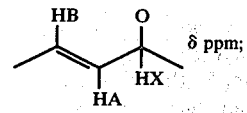

MS: 208 (M+, 43), 193 (35), 161 (87), 133 (25), 119 (42), 105 (57), 91 (39), 85 (33), 69 (26), 59 (100), 41 (38)

EXAMPLE 2

(a) 74.0 g (0.48 mol) of diethyl sulphate were added dropwise to a suspension of β-ionol alcoholate [obtained from 65.8 g (0.34 mol) of β-ionol and 18.4 g (ca 0.44 mol) of 55%–60% sodium hydride in 600 ml of benzene] in such a manner that the temperature did not exceed 50° C. Subsequently, the mixture was stirred at reflux for 3 hours, cooled and worked-up as described in Example 1. Crude distillation of the crude product (72.0 g) gave 50.2 g of crude product which were subsequently purified by distillation over a 20 cm Widmer column. There were obtained 47.0 g ($\triangleq$66.1%) of pure and olfactorily good β-ionyl ethyl ether 2 of boiling point 120°–122° C./10 mmHg.

(b) A solution of 350 g (1.8 mol) of β-ionol in 600 ml of benzene was allowed to flow in over a period of 15 minutes to a suspension of 97.5 g (2.34 mol) of sodium hydride (ca 55%–60%) in 3 liters of benzene and the mixture was subsequently stirred at reflux for 8 hours. The mixture was cooled to ca 50° C. and treated over a period of 10 minutes with 232 g (2.13 mol) of ethyl bromide. The mixture was stirred at reflux for 20 hours, cooled to 20° C., cautiously treated with 50 ml of methanol and, after 20 minutes, with 1.2 liters of water. The phases were separated, the organic phase was washed with water until neutral, dried and concentrated. Crude distillation of the crude product gave 326 g of crude ether 2 of boiling point 120°–128° C./10 mmHg. Fine distillation finally gave 274 g ($\triangleq$68.3%) of pure and olfactorily good β-ionyl ethyl ether 2 of boiling point 121° C./10 mmHg; $n_D^{20}$=1.4752.

IR: 1157, 1135, 1095, 975, 960, 850 cm$^{-1}$;

NMR: 1.00 (6H, 2s); 1.22 (3H, t, J~6.5 Hz); 1.30 (3H, d, J~6.5 Hz); 1.71 (3H, s); 3.50 (2H, m); 3.90 (1H, m); 5.30 (1H, dxd, $J_{HAHX}$~7.5 Hz, $J_{HAHB}$~16 Hz); 6.05 (1H, d, $J_{HAHB}$~16 Hz) δ ppm;

MS: 222 (M+, 66), 207 (47), 161 (93), 133 (30), 121 (55), 105 (63), 91 (52), 73 (60), 55 (41), 43 (100) and further characteristic fragments at m/e 163 (40), 119 (48), 107 (57), 99 (21), 95 (38), 93 (49), 86 (22), 81 (30), 45 (50), 41 (54).

EXAMPLE 3

The alcoholate of β-ionol [obtained from 32.9 g (0.17 mol) of β-ionol and 9.7 g (ca 0.22 mol) of sodium hydride (55%–60%) in 340 ml of benzene] was reacted with 29.5 g (0.24 mol) of isopropyl bromide in a manner analogous to that described in Example 2(b). Fine distillation of the crude distillate gave 19.4 g ($\hat{=}$48.5%) of β-ionyl isopropyl ether 3 of boiling point 82° C./0.08 mmHg.

IR: 1135, 1128, 1075, 995, 972 cm$^{-1}$;

NMR: 1.00 (6H, 2s); 1.15 (6H, d, J~6.5 Hz); 1.29 (3H, d, J~6.5 Hz); ~3.70 (1H, m); ~3.90 (1H, m); 5.30 (1H, dxd, $J_{HAHX}$~7.5 Hz), $J_{HAHB}$~16 Hz); 6.01 (1H, d, $J_{HAHB}$~16 Hz) δ ppm

EXAMPLE 4

The dihydro-β-ionyl methyl ether 5 was prepared in a manner analogous to that described in Example 1 from 48.2 g (0.25 mol) of dihydro-β-ionol, 13.4 g (ca 0.32 mol) of sodium hydride (55%–60%), 44.1 g (0.35 mol) of dimethyl sulphate and the corresponding amount of benzene as the solvent. Fine distillation of the crude distillate (46.2 g) gave 34.1 g ($\hat{=}$65%) of olfactorily good product 5 of boiling point 65°–66° C./0.03 mmHg.

IR: 1202, 1169, 1139, 1091 cm$^{-1}$;

NMR: 1.02 (6H, 2s); 1.18 (3H, d, J~6.5 Hz); 1.61 (3H, s); 3.35 (1H, m); 3.37 (3H, s) δ ppm;

MS: 210 (M+, 7), 163 (21), 136 (11), 123 (47), 107 (22), 93 (26), 85 (36), 72 (100), 59 (60), 41 (28).

EXAMPLE 5

The dihydro-β-ionyl ethyl ether 6 was prepared in a manner analogous to that described in Example 2(a) from 50.0 g (0.255 mol) of dihydro-β-ionol, 13.8 g (ca 0.32 mol) of sodium hydride (55%–60%), 59.4 g (0.386 mol) of diethyl sulphate and the corresponding amount of benzene as the solvent. Fine distillation of the crude distillate (47.8 g) over a 20 cm Widmer column gave 41.6 g ($\hat{=}$72.8%) of olfactorily good product 6 of boiling point 69°–70° C./0.03 mmHg.

IR: 1170, 1130, 1090, 1065 cm$^{-1}$;

NMR: 1.00 (6H, 2s); 1.17 (3H, d, J~6.5 Hz); 1.20 (3H, t, J~6.5 Hz); 1.60 (3H, s); 3.50 (2H+1H, m) δ ppm;

MS: 224 (M+, 8), 163 (53), 123 (70), 121 (47), 107 (55), 99 (54), 95 (44), 93 (52), 86 (100), 81 (52), 73 (60), 55 (31), 45 (55)

EXAMPLE 6

The α-ionyl methyl ether 7 was prepared in a manner analogous to that described in Example 1 from 32.9 g (0.17 mol) of α-ionol, 9.2 g (ca 0.22 mol) of sodium hydride (55%–60%), 30.3 g (0.24 mol) of dimethyl sulphate and the corresponding amount of benzene as the solvent. Fine distillation of the crude distillate (28.0 g) over a 20 cm Widmer column gave 23.6 g ($\hat{=}$66.7%) of olfactorily good α-ionyl methyl ether 7 of boiling point 56°–57° C./0.02 mmHg.

IR: 1203, 1148, 1118, 1098, 975 cm$^{-1}$;

NMR: 0.84 (s, split-up, 3H); 0.88 (3H, s); 1.20 (3H, d, J~6.5 Hz); 1.57 (3H); 3.23 (3H, s); 3.68 (1H, m); 5.37 (3H, m) δ ppm.

MS: 208 (M+, 2), 152 (38), 137 (46), 120 (33), 105 (28), 93 (17), 91 (17), 85 (15), 80 (24), 59 (100), 43 (32).

EXAMPLE 7

The cis-β-ionyl methyl ether 13 was prepared in a manner analogous to that described in Example 1 from 4.8 g (0.025 mol) of cis-β-ionol, 1.35 g (ca 0.032 mol) of sodium hydride (55%–60%), 4.42 g (0.035 mol) of dimethyl sulphate and the corresponding amount of benzene as the solvent. Fine distillation of the crude distillate (5.0 g) gave 3.3 g (63.5%) of olfactorily good cis-β-ionyl methyl ether of boiling point 55°–57° C./0.03 mmHg.

IR: 1204, 1140, 1118, 1111, 1082, 1038 cm$^{-1}$;

NMR: 1.00 (6H, 2s); 1.18 (3H, d, J~6.5 Hz); 1.58 (3H, s); 3.28 (3H, s); 3.82 (1H, m); 5.43 (1H, dxd, $J_{HAHX}$~8 Hz, $J_{HAHB}$~12 Hz); 5.96 (1H, d, J~12 Hz) δ ppm;

MS: 208 (M+, 11), 193 (16), 176 (34), 161 (100), 133 (24), 119 (38), 105 (57), 91 (44), 85 (23), 59 (63), 41 (39).

EXAMPLE 8

The isomethyl-α-ionyl methyl ether 15 was prepared in a manner analogous to that described in Example 1 from 10.0 g (0.048 mol) of isomethyl-α-ionol, 2.6 g (ca 0.061 mol) of sodium hydride (55%–60%), 8.4 g (0.067 mol) of dimethyl sulphate and the corresponding amount of benzene as the solvent. Fine distillation of the crude distillate (7.8 g) gave 6.7 g (63%) of olfactorily good isomethyl-α-ionyl methyl ether of boiling point 60°–61° C./0.01 mmHg.

IR: 1202, 1120, 1100, 1080, 860, 812 cm$^{-1}$;

NMR: 0.80+0.85 (2s, together 3H); 0.94 (3H, s); 1.25 (3H, d, J~6.5 Hz); 1.60 (2×3H); 2.52 (1H, d, J~11 Hz); 3.20 (3H, s); 3.72 (1H, q, J~6.5 Hz); 5.20 (1H, d, J~11 Hz); 5.40 (1H, m) δ ppm;

MS: 222 (M+, 9), 166 (100), 151 (74), 137 (21), 134 (23), 119 (37), 107 (29), 99 (8), 91 (19), 86 (39), 59 (47), 41 (14).

EXAMPLE 9

The β-ionyl allyl ether 16 was prepared in a manner analogous to that described in Example 2(b) from 30.0 g (0.155 mol) of β-ionol, 8.35 g (ca 0.20 mol) of sodium hydride (55%–60%), 26.6 g (0.22 mol) of allyl bromide and the corresponding amount of benzene as the solvent. Fine distillation of the crude distillate (24.3 g) gave 20.3 g (56%) of β-ionyl allyl ether of boiling point 79° C./0.05 mmHg.

IR: 1650, 1140, 1105, 1075, 972, 918 cm$^{-1}$;

NMR: 1.00 (6H, 2s); 1.30 (3H, d, J~6.5 Hz); 1.69 (3H, s); 3.9–4.1 (3H); 5.0–6.2 (5H) δ ppm.

MS: 234 (M+, 9), 175 (39), 163 (49), 135 (53), 133 (48), 123 (40), 107 (41), 95 (42), 81 (32), 69 (35), 43 (100) and further well-defined fragments at m/e 161 (25), 121 (32), 119 (32), 109 (22), 105 (30), 93 (38), 91 (28), 41 (47).

EXAMPLE 10

The isomethyl-α-ionyl ethyl ether 18 was prepared in a manner analogous to that described in Example 2(a) from 27.0 g (0.13 mol) of isomethyl-α-ionol, 7.1 g (ca 0.17 mol) of sodium hydride (55%–60%), 29.3 g (0.19 mol) of diethyl sulphate and the corresponding amount of benzene as the solvent. Fine distillation of the crude distillate (25.1 g) gave 22.1 g (72%) of olfactorily good isomethyl-α-ionyl ethyl ether of boiling point 79° C./0.04 mmHg.

IR: 1110, 1092, 1075, 965, 812 cm$^{-1}$;

NMR: 0.78+0.83 (2s, together 3H); 0.92 (3H, s); 1.18 (3H, t, J~6.5 Hz); 1.23 (3H, d, J~6.5 Hz); ~1.60 (2×3H); 2.47 (1H, d, J~11 Hz); ~3.3 (2H, m); 3.80 (1H, q, J~6.5 Hz); 5.15 (1H, d, J~11 Hz); 5.28 (1H, m) δ ppm;

MS: 236 (M+, 5), 180 (55), 165 (34), 136 (24), 119 (26), 109 (31), 107 (34), 100 (35), 91 (26), 73 (41), 45 (40), 43 (100).

EXAMPLE 11

The α-iryl methyl ether 9 was prepared in a manner analogous to that described in Example 1 from 50.6 g (0.243 mol) of α-irol (obtainable by reducing α-irone with lithium aluminium hydride or sodium borohydride), 12.4 g (ca 0.30 mol) of sodium hydride (55%–60%), 39.6 g (0.314 mol) of dimethyl sulphate and the corresponding amount of benzene as the solvent. Fine distillation of the crude distillate (42.7 g) over a 30 cm Widmer column gave 32.0 g (≙ 59%) of olfactorily good α-iryl methyl ether of boiling point 63°–65° C./0.04 mmHg. This ether was a mixture of the cis- and trans-isomers in the approximate ratio of 1:1.

Cis-isomer:
IR: 1200, 1109, 1082, 992, 981, 910, 839, 792 cm$^{-1}$;
MS: 222 (M+, 4), 152 (100), 137 (76), 120 (33), 105 (24), 91 (15), 85 (8), 80 (19), 59 (56), 55 (14), 43 (14)

Trans-isomer:
IR: 1201, 1119, 1097, 1050, 972, 910, 840, 804 cm$^{-1}$;
MS: 222 (M+, 3), 152 (100), 137 (91), 120 (44), 105 (29), 91 (19), 85 (14), 80 (20), 59 (51), 55 (14), 43 (14).

EXAMPLE 12

The acid-catalysed reaction of 3,7-dimethyl-non-1-yn-6-en-3-ol with isopropenyl methyl ether and subsequent base-catalysed isomerisation of the resulting β-keto-allene [see G. Saucy, R. Marbet, Helv. 50, 1158 (1967)] yielded in good yield 6,10-dimethyl-dodeca-3,5,9-trien-2-one which was cyclised in a known manner [see H. Rouvé, M. Stoll, Helv. 30, 2216 (1947)] with 85% phosphoric acid to give 12/13-methyl-α-ionone. Subsequent reduction with lithium aluminium hydride gave 12/13-methyl-α-ionol.

The 12/13-methyl-α-ionyl methyl ether 10 was prepared in a manner analogous to that described in Example 1 from 60.1 g (0.29 mol) of 12/13-methyl-α-ionol, 14.8 g (0.354 mol) of sodium hydride (55%–60%), 47.1 g (0.373 mol) of dimethyl sulphate and the corresponding amount of benzene as the solvent. Fine distillation of the crude distillate (47.2 g) over a 15 cm Widmer column gave 39.0 g (≙ 61%) of olfactorily good 12/13-methyl-α-ionyl methyl ether of boiling point 89° C./0.04 mmHg.

IR: 1200, 1117, 1098, 975, 820 cm$^{-1}$;
NMR: 0.80 (3H, s); 0.83 (3H, t, J~5 Hz); 1.20 (3H, d, J~6.5 Hz); 1.59 (3H, s); 3.23 (3H, s); 3.70 (1H, m); 5.2-5.5 (3H, m) δ ppm;
MS: 222(M+, 20), 193 (21), 152 (95), 137 (80), 120 (42), 105 (32), 91 (23), 85 (17), 80 (18), 59 (100), 45 (9), 43 (18).

EXAMPLE 13

The cyclisation of 6-ethyl-7,10-dimethylundeca-3,5,9-trien-2-one (obtained in a manner analogous to that described in Example 12) with 85% phosphoric acid yielded a crude product which contained more than 90% of 3,11-dimethyl-α-ionone and 3,11-dimethyl-γ-ionone (2 isomers) in the approximate ratio of 7:3. Subsequent reduction with lithium aluminium hydride gave 3,11-dimethyl-α-ionol, together with 3,11-dimethyl-γ-ionol.

The 3,11-dimethyl-α-ionyl methyl ether 11 was prepared in a manner analogous to that described in Example 1 from 33.7 g (0.152 mol) of the foregoing alcohols, 7.76 g (0.186 mol) of sodium hydride (55%–60%), 24.7 g (0.196 mol) of dimethyl sulphate and the corresponding amount of benzene as the solvent. Fine distillation of the crude distillate (25.5 g) over a 20 cm Widmer column gave 22.7 g (≙ 63%) of olfactorily good product of boiling point 72°–74° C./0.04 mmHg. This product contained more than 90% of 3,11-dimethyl-α-ionyl methyl ether and the corresponding γ-isomer in the approximate ratio of 7:3.

IR: 1200, 1115, 1097, 972, 842, 820 cm$^{-1}$;
NMR: 0.82 (3H, t, J~5 Hz); 0.85 (6H, 2s); 1.22 (3H, d, J~6.5 Hz); 1.62 (3H, s); 3.24 (3H, s); 3.68 (1H, m); 5.2-5.5 (2H, m) δ ppm;
MS: 236 (M+, 39), 180 (63), 165 (53), 151 (51), 148 (35), 140 (29), 133 (29), 121 (42), 108 (46), 93 (38), 85 (18), 59 (100).

The following Examples illustrate odorant and/or flavouring compositions provided by the present invention:

EXAMPLE A

Fruit complex containing β-ionyl ethyl ether

|  | Parts by weight |
|---|---|
| Dimethylbenzylcarbinyl butyrate | 100 |
| Allylionone | 80 |
| Fructone (Trademark) IFF ethyleneglycol ketal of ethyl acetoacetate) | 60 |
| Palmarosa oil | 40 |
| γ-Undecalactone | 30 |
| Galaxolide 50 (Trademark) (1,3,4,6,7,8-hexahydro-4,6,6,7,8,8-hexamethyl-cyclopenta-γ-2-benzopyran) | 20 |
| Dipropyleneglycol | 600 |
|  | 930 |

When there are added to this fruit complex (a complex having conventional apricot character) 70 parts of β-ionyl ethyl ether, then there is obtained a much more natural apricot odour. The total complex now has an agreeable freshness, and balance and satisfies modern perfumery which is striving for naturality.

EXAMPLE B

Fruit complex containing α-ionyl methyl ether

|  | Parts by weight |
|---|---|
| Dimethylbenzylcarbinyl butyrate | 100 |
| Allylionone | 80 |
| Fructone (Trademark) IFF (2-methyl-1,3-dioxolan-2-ethyl acetate) | 60 |
| Palmarosa oil | 40 |
| γ-Undecalactone | 30 |
| Galaxolide 50 (Trademark) | 20 |
| Dipropyleneglycol | 600 |
|  | 930 |

Addition of 70 parts of α-ionyl methyl ether to this fruit complex having conventional apricot character brings about an extremely interesting modification in the direction of a dried fruit complex.

EXAMPLE C

Perfumery composition having violet character

|  | Parts by weight |
|---|---|
| Raldeine (methylionone) | 300 |
| Phenylethyl alcohol | 200 |
| Benzyl acetate | 100 |
| Hydroxycitronellal | 80 |
| Heptynecarboxylic acid methyl ester (10% in propyleneglycol) | 40 |
| Iris concrete | 40 |
| Rhodinol extra | 40 |
| Ylang-ylang oil | 40 |
| Nerol extra | 40 |
| Heliotropin | 40 |
|  | 920 |

When there are added to this composition 80 parts of β-ionyl ethyl ether, then the violet note is underlined in an advantageous manner and the total composition gains in fullness and radiation power.

EXAMPLE D

When there are added to the composition described in Example C 80 parts of α-ionyl methyl ether, then there is surprisingly obtained a very flowery-fresh composition in the direction of gardenia.

EXAMPLE E

Chypre composition containing β-ionyl ethyl ether

|  | Parts by weight |
|---|---|
| Methyl 1-methylcyclododecyl ether | 150 |
| Bergamotte oil | 150 |
| Bornyl acetate | 120 |
| Hydroxycitronellal | 100 |
| Galaxolide 50 (Trademark) IFF | 100 |
| Linalool synthetic | 80 |
| Citronellol extra | 60 |
| Nerol extra | 50 |
| Patchouli oil | 50 |
| Tree moss absolute | 30 |
| Cedryl acetate crystalline | 30 |
| Lemon oil | 30 |
| Styrallyl acetate | 20 |
|  | 970 |

Addition of 30 parts of β-ionyl ethyl ether enriches this conventional chypre composition with a very agreeably acting, fruity note. The composition is now sweeter, more full, more powerful and, in toto, significantly feminine. The bottom note attracts attention by an agreeable, warm, spicy wood note.

EXAMPLE F

Chypre composition containing α-ionyl methyl ether

When there are added to the chypre composition described in Example 18 30 parts of α-ionyl methyl ether, then the fresh lemon note thereof is distinctly underlined. The composition now is more lively, more diffuse and has a masculine character.

EXAMPLE G

Cologne base containing isomethyl-α-ionyl methyl ether

|  | Parts by weight |
|---|---|
| Bergamotte oil | 200 |
| Hydroxycitronellal | 160 |
| Linalool synthetic | 160 |
| Methyl dihydrojasmonate | 80 |
| Methyleugenol | 80 |
| Vertofix (Trademark) IFF (acetylcedrene) | 60 |
| Acetanisole | 40 |
| Musc 174 (Trademark) (12-oxahexadecanolid) | 40 |
| Petitgrain oil | 40 |
| Bornyl acetate | 20 |
| Basil oil | 20 |
|  | 900 |

Addition of 100 parts of the novel compound brings about in the foregoing cologne base a great increase in the intensity and diffusion. The complex bergamotte-basil, which does not come into play in the original base, supplies to the novel base a very original note.

EXAMPLE H

Perfumery base having a green note and containing isomethyl-α-ionyl methyl ether

|  | Parts by weight |
|---|---|
| Petitgrain oil Paraguay | 100 |
| Galbanum oil | 100 |
| Musc 174 (Trade Mark) | 100 |
| Bergamotte oil | 60 |
| Angelica seed oil | 40 |
| Propyleneglycol | 400 |
|  | 800 |

When there are added to this green base, which is not well suited for modern Eau de Cologne, 200 parts of the novel compounds, then the base is rounded-off in an advantageous manner. The sought for galbanum note is underlined and simultaneously the fresh top note of the bergamotte oil is better recognised, the composition is more diffuse.

EXAMPLE I

Flower base containing isomethyl-α-ionyl methyl ether

|  | Parts by weight |
|---|---|
| Phenylethyl alcohol | 200 |
| Eugenol | 100 |
| Isoeugenol | 100 |
| Geraniol pure | 150 |
| Citronellol extra | 100 |
| Hydroxycitronellal | 100 |
| Jasmine synthetic | 100 |
| Amyl salicylate | 80 |
| Methyl dihydrojasmonate | 20 |
|  | 950 |

When there are added to this unspecific flower complex 50 parts of the novel compounds, then a pronounced "perfumistic" flower composition comes nearer; the addition brings about an agreeable rounding-off effect. The resulting composition is finer and brings about conversion of the generally unspecific direction to a pronounced jasmine-ylang note.

EXAMPLE J

Perfumery base (rose direction) containing α-iryl methyl ether or 12/13-methyl-α-ionyl methyl ether

|  | Parts by weight |
|---|---|
| Phenylethyl alcohol | 460 |
| 2-Ethyl-3,6,6-trimethyl-2-cyclohexen-1-yl-carboxylic acid ethyl ester | 100 |
| Geraniol | 100 |
| Citronellol | 100 |
| α-Ionone | 40 |
| Cinnamic alcohol substitute | 100 |
|  | 900 |

When there are added to this "simple" rose base 100 parts of α-iryl methyl ether, then the base is more rounded-off and complete, and it takes on a slightly woody rhodinol note which gives the base the required nuance in the direction of strong red roses.

On the other hand, when there are added to the foregoing rose base 100 parts of 12/13-methyl-α-ionyl methyl ether, then the rose base is improved in the direction of tea (yellow) roses. The base acts more powerfully, sweeter and the citronellol is underlined.

EXAMPLE K

Woody-fresh perfumery base for the perfuming of soaps

|  | Parts by weight |
|---|---|
| Bornyl acetate | 520 |
| Galaxolide 50 (Trade Mark) | 100 |
| Methylnonylacetaldehyde (10% in propyleneglycol) | 60 |
| Frankincense resinoid | 60 |
| p-tert Butyl-cyclohexyl acetate | 60 |
| Linalyl anthranilate | 40 |
| Lavandin oil | 40 |
| Heliotropin | 20 |
|  | 900 |

When there are added to a soap mass of the usual composition 1.5% of the aforementioned fresh-woody base, then there is obtained a modern fresh soap. When 100 parts of 12/13-methyl-α-ionyl methyl ether 10 are added to this base, then the soap produced with the new base is more powerful; the bornyl acetate is underlined and the fresh effect is increased. There is produced a soap in the direction of the Rexona type.

On the other hand, when 100 parts of the 3,6,6-trimethyl-2-ethyl-1-(3'-methoxy-1-butenyl)-cyclohex-2-ene ether 11 are added to the base, then the lavandin note is underlined and now a more natural effect is obtained. The impression of apple blossom predominates in the bottom note. This base can therefore also be used very well in the production of shampoos.

EXAMPLE L

Perfumery base containing 3,6,6-trimethyl-2-ethyl-1-(3'-methoxy-1-butenyl)-cyclohex-2-ene

|  | Parts by weight |
|---|---|
| Benzyl acetate | 120 |
| α-Ionone | 120 |
| α-Hexylcinnamaldehyde substitute | 120 |
| Linalool | 100 |
| Methyl 1-methylcyclododecyl ether | 80 |
| Benzyl salicylate | 60 |
| p-tert.Butyl-cyclohexyl acetate | 60 |
| Citronellol | 60 |
| Galaxolide 50 (Trademark) | 40 |
| Terpenyl acetate | 40 |
| Eugenol | 40 |
| Phenylethyl alcohol | 20 |
| Petitgrain oil | 20 |
| Citral | 6 |
| Coumarin | 6 |
| Indole (10% in ethanol) | 4 |
| Vanillin | 4 |
|  | 900 |

When there is added to a washing powder 0.2% of this perfumery base, then there is obtained a "flowery-fresh" was agent. When there are now added to the base 100 parts of the novel compound, then the thus-perfumed washing agent has a more powerful odour. Its fixative note is increased and the bottom note has a strongly powdery character.

EXAMPLE M

Raspberry flavour containing β-ionyl ethyl ether

|  | A | B |
|---|---|---|
| Ethyl palmitate | 0.05 | 0.05 |
| Geraniol | 0.2 | 0.2 |
| Methylionone | 0.6 | 0.6 |
| Ethylvanillin | 1.0 | 1.0 |
| Amyl valerate | 1.0 | 1.0 |
| Maltol | 2.0 | 2.0 |
| Benzyl acetate | 2.0 | 2.0 |
| Dimethylsulphide (10% in propyleneglycol) | 2.0 | 2.0 |
| Aldehyde C-16 | 2.5 | 2.5 |
| Ethyl formate | 4.0 | 4.0 |
| Hexyl butyrate | 5.0 | 5.0 |
| Raspberry ketone | 5.0 | 5.0 |
| Amyl acetate | 6.0 | 6.0 |
| Ethyl butyrate | 6.0 | 6.0 |
| Isobutyl acetate | 23.0 | 23.0 |
| Ethyl acetate | 33.5 | 33.5 |
| Propyleneglycol | 906.15 | 896.15 |
| β-Ionyl ethyl ether (10% in ethanol) |  | 10.0 |
|  | 1000.00 | 1000.00 |

Addition of β-ionyl ethyl ether to composition A (a conventional raspberry flavour alters the odour in an advantageous manner.) The pronounced ester-like note of A is now, in B, enriched by a typical fruity note. The composition possesses substantially more fullness and radiance.

Regarding taste, a clear improvement is likewise ascertainable using 100 g of flavourant per 100 liters of sugar syrup, diluted 1:5 with water, in that the typical fruity note for raspberry appears stronger in the treated sugar syrup.

EXAMPLE N

β-Ionyl ethyl ether as a tobacco additive 100 g of Maryland tobacco were sprayed evenly with 3 ml of a 1% solution of β-ionyl ethyl ether in ethanol and subsequently stored at room temperature for 24 hours. The cigarettes produced from the thus-treated tobacco showed, upon smoking, a pleasant woody-flowery note in comparison to untreated cigarettes (blank sample). Moreover, the flavour of the smoke was milder and more rounded-off.

EXAMPLE O

Dihydro-β-ionyl ethyl ether as a tobacco additive

In the manner described in Example N, 100 g of Maryland tobacco were treated with 2 ml of a 1% solution of dihydro-β-ionyl ethyl ether in ethanol. The cigarettes produced from the thus-treated tobacco showed, upon smoking, a pleasant cedarous-woody note, accompanied by a slightly flowery note, in comparison to the blank sample. Moreover, the flavour of the smoke was softer and more rounded-off.

What is claimed is:

1. A tobacco to which there has been added an effective amount of a compound, in a range of from one part per million to one thousand parts per million, of the general formula

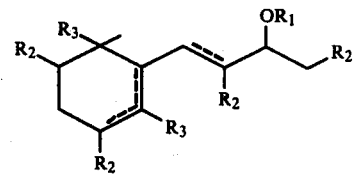

wherein $R_1$ represents a $C_{1-4}$-alkyl or $C_{2-4}$-alkenyl group, $R_2$ represents a hydrogen atom or the methyl group, $R_3$ represents the methyl or ethyl group, the broken line in the side chain represents an optional bond and one of the broken lines in the ring represents an additional bond.

2. A tobacco in accordance with claim 1 wherein 2,6,6-trimethyl-1-(3-ethoxy-1-butenyl)-cyclohex-1-ene is added in an amount effective to add a pleasant woody and slightly flowery note to the tobacco smoke.

3. A tobacco in accordance with claim 2 wherein the compound is present in a range of from fifty parts per million to five hundred parts per million.

4. A tobacco in accordance with claim 1 wherein the compound is present in a range of from one hundred parts per million to one thousand parts per million.

5. A tobacco in accordance with claim 1 wherein the compound is present in a range of from one hundred parts per million to five hundred parts per million.

* * * * *